United States Patent [19]

Kutner et al.

[11] Patent Number: 5,019,344
[45] Date of Patent: May 28, 1991

[54] METHOD FOR STERILIZING ARTICLES SUCH AS DENTAL HANDPIECES

[75] Inventors: Barry S. Kutner, Wilton; Daniel A. Latowicki, Newtown, both of Conn.

[73] Assignee: Flexiclave, Inc., Del.

[21] Appl. No.: 184,246

[22] Filed: Apr. 21, 1988

[51] Int. Cl.⁵ ............................................. A61L 2/12
[52] U.S. Cl. ........................... 422/21; 219/10.55 E; 250/455.1; 422/28; 422/32; 422/33; 422/294; 422/299
[58] Field of Search .................. 422/21, 22, 28, 32, 422/33, 294, 288, 299, 305; 250/455.1; 426/107, 234, 243; 219/10.55 E

[56] References Cited

U.S. PATENT DOCUMENTS

| | | |
|---|---|---|
| 3,261,140 | 7/1966 | Long et al. ............................. 422/21 |
| 3,490,580 | 1/1970 | Brumfield et al. .................... 422/21 |
| 3,494,726 | 2/1970 | Barasch ................................. 422/29 |
| 3,551,090 | 12/1970 | Brumfield et al. .................... 422/21 |
| 3,753,651 | 8/1973 | Boucher ................................. 422/21 |
| 4,400,357 | 8/1983 | Hohmann ............................ 422/299 |

FOREIGN PATENT DOCUMENTS 3505571 8/1986 Fed. Rep. of Germany ........ 422/21
80/413 3/1980 World Int. Prop. O. ............ 422/21

*Primary Examiner*—Robert J. Warden
*Assistant Examiner*—Timothy M. McMahon
*Attorney, Agent, or Firm*—Steinberg & Raskin

[57] ABSTRACT

Method and apparatus for sterilizing articles such as dental handpieces include introducing the article and liquid sterilant solution into a collapsible pouch formed of vapor-impermeable sheet material, sealing the collapsible pouch to form a gas-tight assembly, and heating the gas-tight assembly to vaporize the liquid sterilant solution to produce an atmosphere of hot sterilant vapor. The liquid sterilant is introduced into the pouch in a quantity sufficient to create an overpressure when vaporized which is indicated by the collapsible pouch expanding to a distended condition. In one embodiment, the liquid sterilant solution is vaporized by irradiating the gas-tight assembly with microwave radiation in which case the article is sterilized under the combined effects of chemical vapor and microwave irradiation.

8 Claims, 3 Drawing Sheets

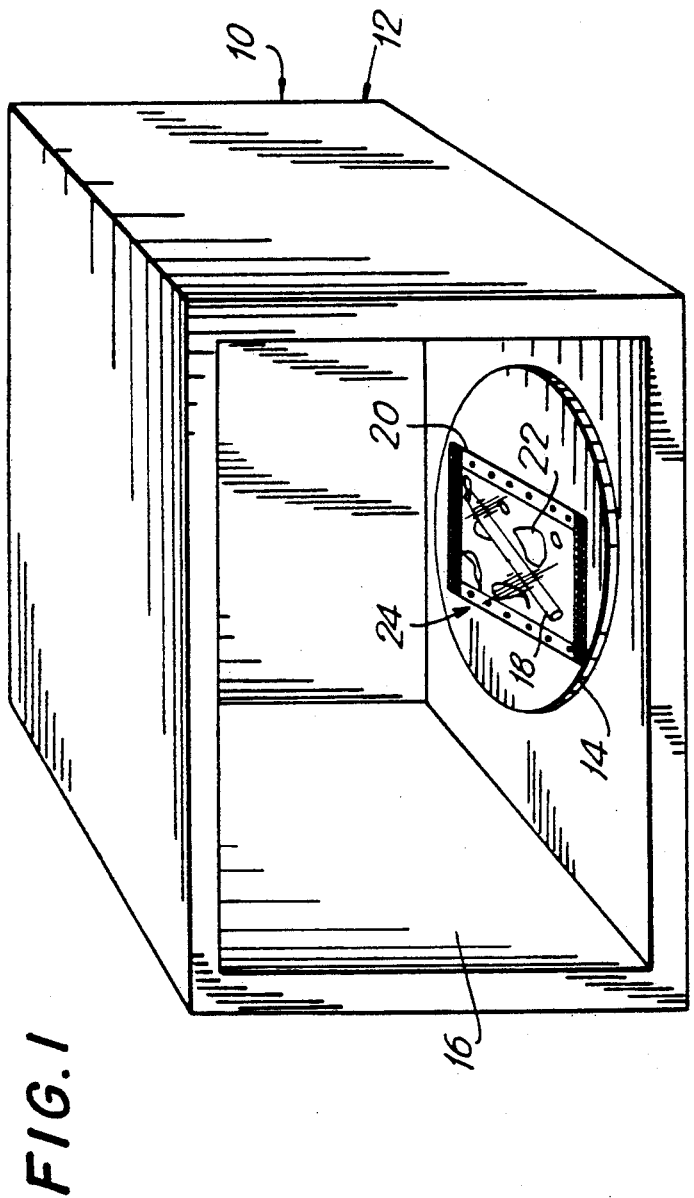
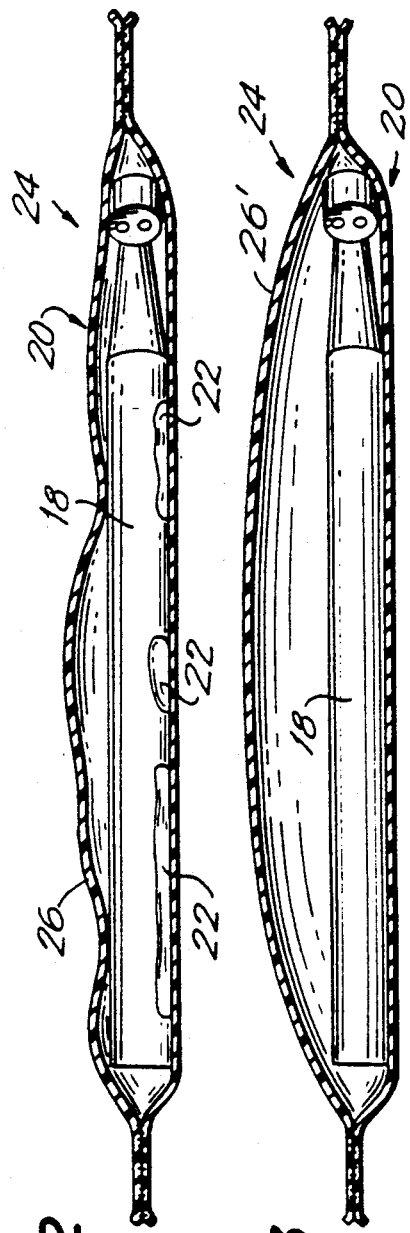
FIG.1
FIG.2
FIG.3

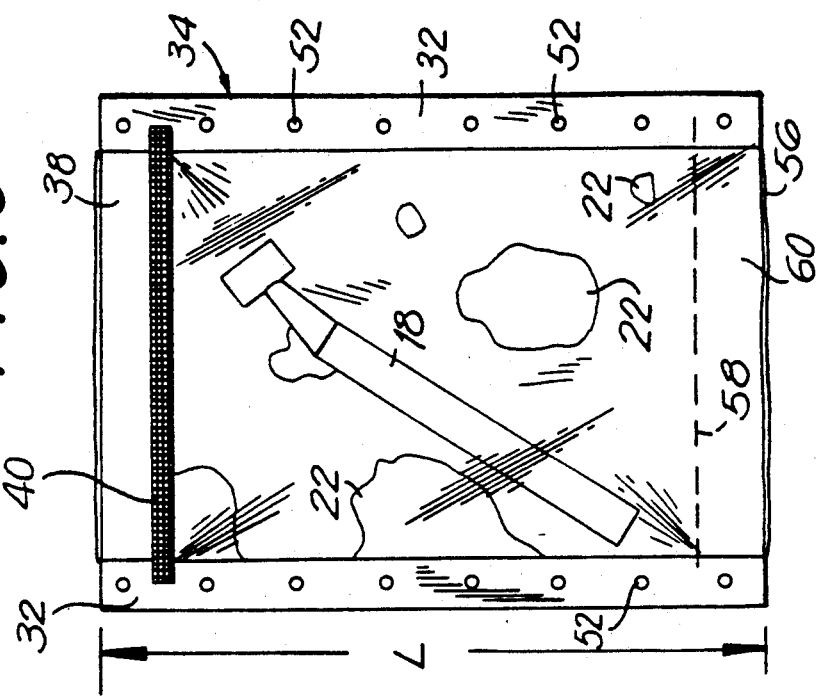
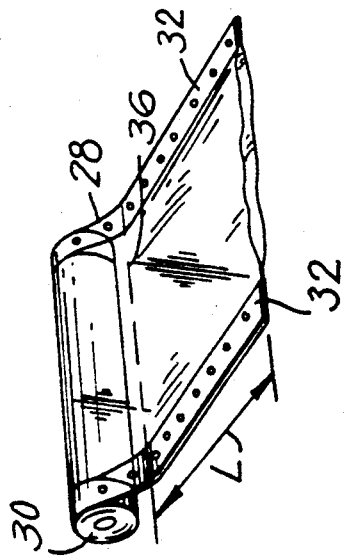
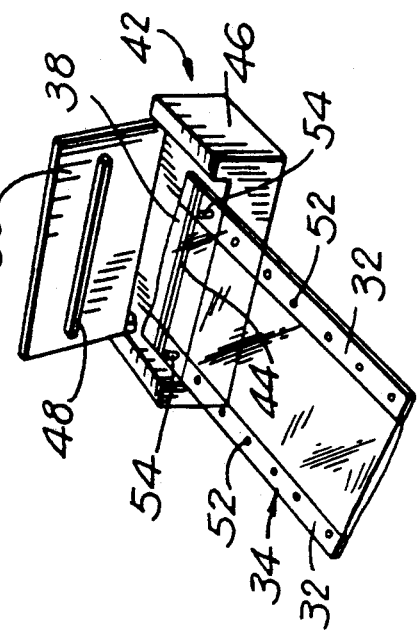

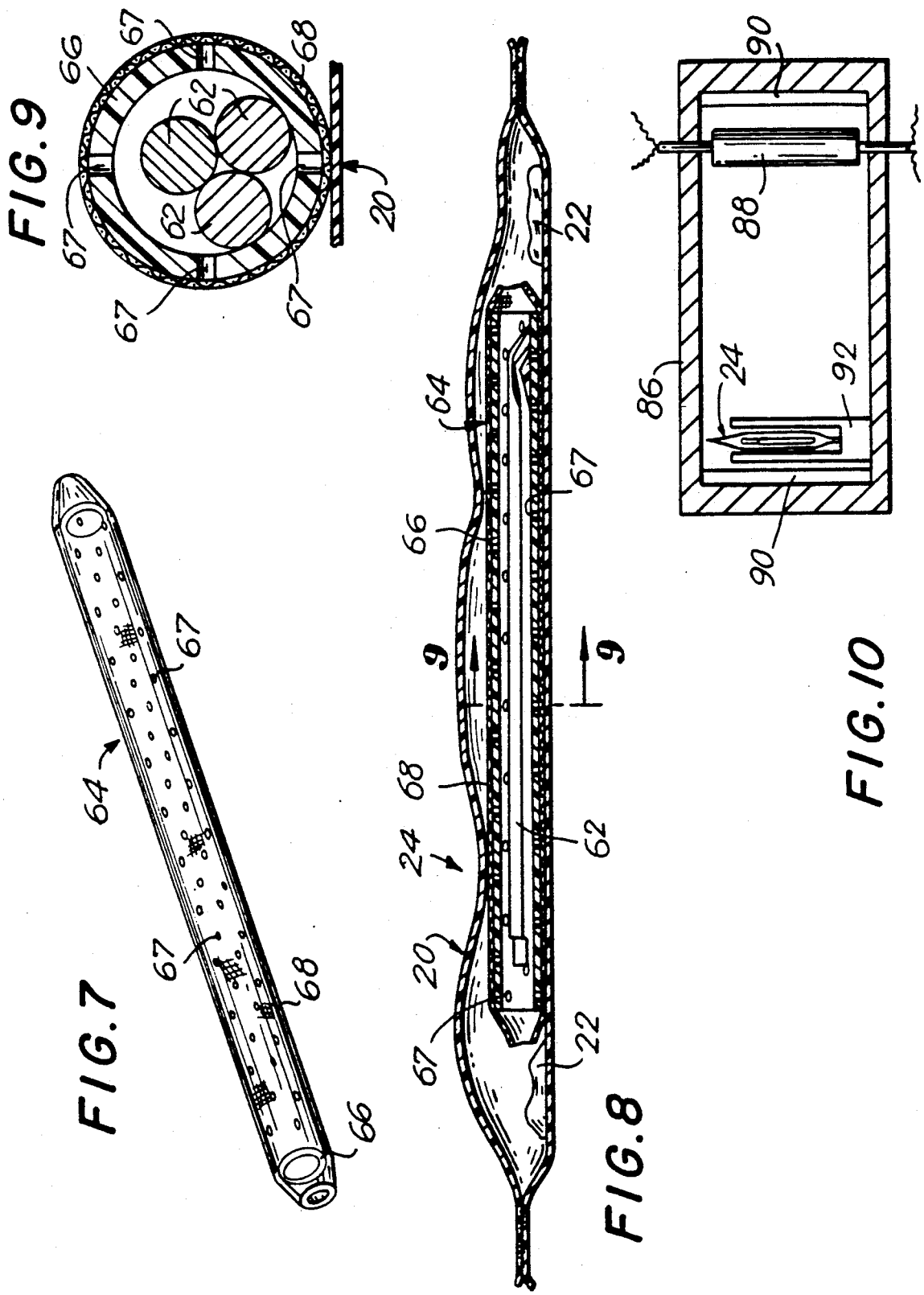

METHOD FOR STERILIZING ARTICLES SUCH AS DENTAL HANDPIECES

BACKGROUND OF THE INVENTION

This invention relates generally to methods and apparatus for sterilizing articles, and more particularly, to methods and apparatus for sterilizing dental and other medical instruments, such as dental handpieces.

The need for effective sterilization of dental instruments, such as dental handpieces, is more important today than ever before due to the realization of the significant potential for infection via dental procedures and the increase in the rate of transmission of serious diseases by blood and saliva. However, from a practical viewpoint, not only must the sterilization procedure be effective, it must also be rapid, i.e., have a short turn-around or cycle time. Thus, it will be understood that the quantity of any one instrument that a practitioner or institution must purchase and have available for use will depend on the frequency of treatments requiring that instrument and on the turn-around time required to sterilize the instrument. In the case of dental handpieces, which generally are required for most treatments performed in the dental operatory, an extended sterilization cycle means that a larger inventory of available handpieces must be maintained. The high cost of dental handpieces, on the other hand, often limits the number of available handpieces, which in turn may result in hasty and therefore ineffective attempts at, or even dispensing with, lengthy sterilization procedures. This of course is unacceptable.

Heat sterilization methods, such as steam heat (autoclave), dry heat, and chemical vapor, are generally preferred over cold immersion methods, which are generally not effective unless glutaraldehyde is used and the instrument is immersed for 7–10 hours. Chemical vapor sterilization has the advantages of minimal corrosion of burs and other sharp instruments (steam sterilization or immersion in most liquid disinfectants produces dullness and rusting) and a cycle time which is relatively short compared to cold sterilization techniques.

One type of chemical vapor sterilizer which is in commercial use (available from MDT Corporation of Gardena, Calif. under the designation Harvey Chemiclave) comprises a sterilizer which uses moderate heat (about 270° F.), pressure (about 20 psi) and a special solution composed primarily of 3A alcohol (about 80%) and water (about 9%) with small amounts of acetone, ketone and formaldehyde. The sterilization time is about 20 minutes after proper pressure is reached. The length of time required to reach pressure depends on the size of the load. On the other hand, the purchase price of this arrangement is higher than steam and dry heat processors. Additional drawbacks are that relatively large quantities of sterilizing solution are required, and odor and minor irritation of eyes, nose and throat from chemical vapors often accompanies use, the sterilizing chamber must be cleaned on a frequent basis, the instruments should be wrapped to preserve sterility, and the simultaneous sterilization of a plurality of instruments results in the possibility of cross-contamination. Moreover, the sterilization cycle time, although less than the time required for the sterilization by solution immersion, is still relatively long, essentially because of the relative great chamber volume.

U.S. Pat. No. 4,400,357 issued Aug. 23, 1983 to Hohmann, discloses an arrangement for chemical vapor sterilization of articles, such as dental handpieces, which would appear to overcome some of the above-mentioned problems. The patent discloses an arrangement in which the article to be sterilized is situated in an enlarged portion of a rigid vessel. A liquid reaction agent is charged into a narrow portion of the vessel which is in communication with the enlarged article-containing vessel portion. The liquid reaction agent is heated to produce a vapor which flows into the first vessel portion to sterilize the article. The first vessel portion may be designed to accept only a single article in which case the amount of liquid reaction agent required to generate the vapor is relatively small which in turn reduces the heating time required for vaporization and the overall sterilization cycle time. The patent suggests that the means for heating the liquid reaction agent may comprise a microwave radiator. In this case, the vessel is situated such that only the narrow liquid-containing vessel portion is subjected to the microwave radiation while the article to be sterilized is kept outside the radiation field which, the patent notes, avoids the formation of spark gaps at border surfaces and seams of the article which cause surface destruction. In any event, although microwave radiation is known to have beneficial sterilizing effects, the patent notes that microwave radiation will not penetrate into the seams and crevises of the article and not kill micro-organisms situated therein. Although possibly reducing the time required for sterilization, the arrangement proposed in the patent has various drawbacks which have apparently prevented adoption and commercialization of this arrangement. For example, it requires a complicated, specially designed microwave generator adapted for positioning the vessel with only the liquid reaction agent-containing portion in the radiation field of the microwave generator with the article-containing vessel portion outside the radiation field. It requires a specially designed rigid vessel which either must be cleaned after each use to avoid cross-contamination or discarded at significant expense. Moreover, the sterilizing effect of the microwave radiation is not utilized since the microwave energy is used only for vaporizing the liquid reaction agent.

A good discussion of the sterilization of articles, such as dental instruments, by microwave radiation is set forth in U.S. Pat. No. 3,753,651 issued Aug. 21, 1973 to Boucher. Briefly, it is noted that sterilization by microwave radiation is due to both thermal effects, such as microwave induced heat, and non-thermal effects, which the patent suggests may affect a metabolic system distinct from that of thermal energy. It is disclosed that improved surface sterilization results are obtained when the articles are subjected to microwave radiation while situated in a humid atmosphere, i.e., an atmosphere having a relative humidity of least 50% or supersaturated with water or saline solution. To this end, the articles to be sterilized are placed on trays which are situated in a rigid, microwave-transparent container having a known volume, along with a quantity of water or saline solution determined by the container volume so as to be sufficient when vaporized to increase the humidity of the atmosphere within the container to the desired value. After placing the articles to be sterilized and the water or saline solution into the container, the container is sealed with a lid and then placed within the cavity of a microwave generator and subjected to microwave radiation. The electro-magnetic energy penetrates through the container walls to evaporate the water or saline solution to produce the desired humidity, and at the same time, proceeds to sterilize the surface of the article by the thermal and non-thermal effects discussed above. It is indicated that this procedure results in reduced cycle time for effective sterilization compared to dry heat or steam sterilizing methods and that the localized arcing (sparking) which usually occurs when metallic objects are irradiated by microwave radiation is practically eliminated in the moist atmosphere.

The patent also points out that the container can be filled with any gas to constitute the atmosphere to be humidified. For example, it is suggested that a gas or vapor sterilant can be introduced into the container through valves provided in the container walls to take advantage of their chemical sterilizing effects, although care should be taken to avoid heating the article being sterilized to a point where it reaches the ignition or explosion point of the gas, The arrangement proposed in U.S. Pat. No. 3,753,651 has drawbacks which have apparently prevented it from being adopted on a practical basis. For example, as noted in the above-discussed U.S. Pat. No. 4,400,357, only surface sterilization is achieved by microwave irradiation and micro-organisms present on surfaces located within the seams and crevices of the article will not be killed, especially if blood and salivary protein are deposited on those surfaces. This is true regardless of whether the container is initially filled with a gas sterilant as suggested in the patent. The procedure requires a specially designed gas-tight rigid container having a known, fixed volume. The container must be sterilized after each use or discarded, in which case considerable expense is incurred especially where valves are provided in the container walls as discussed above. To provide a truly gas-tight condition, it is necessary to use materials, such as for gaskets and the like, which are not entirely transparent to microwaves. Moveover, the relatively large volume of the container which is necessary to accommodate the articles to be sterilized in turn requires a relatively large volume of water or saline solution to achieve the desired humidity. This results in an increase in the time required for the evaporation of the water or saline solution thereby increasing the overall sterilization cycle time.

SUMMARY OF THE INVENTION

It is an object of the present invention to provide new and improved methods and apparatus for sterilizing articles such as dental and medical instruments, particularly dental handpieces.

Another object of the present invention is to provide new and improved methods and apparatus for chemical vapor sterilization of such articles.

Still another object of the present invention is to provide new and improved methods and apparatus for obtaining the advantages of both chemical vapor and microwave sterilization techniques without the disadvantages noted above.

A further object of the present invention is to provide new and improved methods and apparatus for sterilizing one or more metallic articles, including dental instruments and instruments having sharp edges and points in a microwave radiation field without sparking or arcing.

Yet another object of the present invention is to provide new and improved methods and apparatus for effectively sterilizing articles, such as medical and dental articles, using simple, readily available material and equipment and with a cycle time which is significantly reduced relative to prior art arrangements.

Briefly, in accordance with the present invention, these and other objects are attained by providing an arrangement wherein an article to be sterilized is situated within a collapsible pouch formed of flexible sheet material which is vapor-impermeable. The collapsible pouch has an opening which permits insertion of the article into the pouch, the opening being sealable by the user to retain the article in the pouch and to prevent the loss of vapor therefrom. A predetermined quantity of liquid sterilant solution is introduced into the pouch along with the article whereupon the opening is sealed to form a gas-tight assembly. The liquid sterilant is then heated by any suitable means until it vaporizes. In accordance with the invention, the quantity of liquid sterilant solution introduced into the collapsible pouch is sufficient so that upon vaporization, an overpressure is created within the pouch. That the required overpressure has been achieved is visually apparent according to the invention by observation of the walls of the pouch during vaporization of the liquid sterilant solution, the walls flexing outwardly from their initial collapsed condition under the forces of the increasing internal pressure and reaching a fully distended condition upon the internal pressure reaching the required overpressure. The hot sterilant vapor contacts the surfaces of the article under pressure penetrating into the narrow seams and crevices thereof. The article is allowed to remain in the atmosphere of the hot sterilant vapor under pressure for a certain time whereupon it is effectively sterilized.

In one embodiment of the invention, particularly suited for the sterilization of medical instruments such as dental handpieces, after introducing the handpiece and liquid sterilant solution into the pouch and sealing the opening thereof, the thus-formed gas-tight assembly is placed within the cavity of a microwave radiator and subjected to microwave irradiation. In this embodiment, the collapsible pouch is formed of sheet material which, in addition to having the above-mentioned characteristics, is also transparent to microwaves. The liquid sterilant solution is vaporized under the thermal effects of the microwave radiation producing a hot sterilant vapor atmosphere under pressure as described above. At the same time, the handpiece is subjected to microwave radiation. Sterilization of the handpiece is therefore achieved by the thermal and non-thermal effects of microwave radiation as well as by chemical vapor treatment. The combined microwave and chemical vapor sterilization achieves effective and complete sterilization of the dental handpiece in significantly less time than has been possible heretofore. It is noteworthy that, surprisingly, no arcing occurs, despite microwave irradiation, in the course of sterilization of a single dental handpiece according to this procedure.

It is advantageous to utilize microwave energy for vaporizing the liquid sterilant solution within the collapsible pouch in the chemical vapor sterilization technique of the invention due to efficiency and the ready availability of microwave generators. As described above, the combined sterilizing effects of microwave irradiation and chemical vapor can be utilized in the sterilizing of a single dental handpiece according to the invention without the risk of arcing or sparking. However, it would not be possible to sterilize a plurality of handpieces or other instruments situated within the same collapsible pouch in this manner without risking the possibility of arcing or sparking. Indeed, chemical vapor sterilization according to the invention of even a single pointed instrument, such as a dental explorer, may result in arcing where the instrument is subjected to microwave radiation used to heat and vaporize the liquid sterilant solution in the gas-tight assembly.

In accordance with another aspect of the invention, the simultaneous chemical vapor sterilization of a plurality of dental handpieces and/or one or more pointed instruments, situated in the same collapsible pouch, can be accomplished utilizing microwave energy to vaporize the liquid sterilant solution and without the risk of arcing or sparking by preliminarily inserting the instruments into the interior of a shield assembly comprising a holder member formed of electrically insulative material, the outer surface of which is covered by an electromagnetic radiation shield material. The interior of the holder member is open to the ambient atmosphere. The shield assembly containing the one or more instruments is thereupon situated in the collapsible pouch along with the liquid sterilant solution and the gas-tight assembly is formed whereupon the sterilization procedure may proceed by subjecting the gas-tight assembly to microwave irradiation to produce the hot sterilant vapor as described above. The shield assembly eliminates the risk of any sparking or arcing even for instruments having the sharpest points and edges during the sterilization procedure. The hot chemical vapor under pressure passes into the interior of the shield assembly into contact with the one or more instruments to sterilize the same.

According to another aspect of the invention, the collapsible pouch preferably is formed as the first step in the procedure from a section of an elongate tubular web of suitable plastic sheet material, e.g. a pair of overlying sheets presealed along their outer edge margins, and using suitable hot-wire sealing apparatus. In this manner, the size of the pouch can be "customized" for the geometry of the particular article being sterilized.

DESCRIPTION OF THE DRAWINGS

A more complete appreciation of the present invention and many of the attendant advantages thereof will be readily understood by reference to the following detailed description when considered in connection with the accompanying drawings in which:

FIG. 1 is an orthoganal view of apparatus in accordance with the invention;

FIG. 2 is a sectional view taken along line 2—2 of FIG. 1 of a dental handpiece and liquid sterilant solution within a sealed collapsible pouch forming a gas-tight assembly;

FIG. 3 is a sectional view of the gas-tight assembly shown in FIG. 2 after vaporization of the liquid sterilant solution;

FIG. 4 is a perspective view of a roll of two-ply tubular web material used for forming a collapsible pouch;

FIG. 5 is a perspective view of hot-wire sealing apparatus in use forming a collapsible pouch from the two-ply tubular web material shown in FIG. 3;

FIG. 6 is a top plan view of a pouch-forming section of the two-ply tubular web material, one side of which has been sealed and into the opening of which a dental handpiece and liquid sterilant solution have been introduced;

FIG. 7 is a perspective view of a tubular shield assembly in accordance with the invention;

FIG. 8 is a sectional view of a gas-tight assembly including a collapsible pouch containing liquid sterilant solution and a tubular shield assembly holding a plurality of instruments to be sterilized;

FIG. 9 is a sectional view taken along line 9—9 of FIG. 8; and

FIG. 10 is a front elevation view of another embodiment of apparatus in accordance with the invention.

DETAILED DESCRIPTION OF THE PREFERRED EMBODIMENTS

Referring now to the drawings wherein like reference characters designate identical or corresponding parts throughout the several views, and more particularly to FIGS. 1-3, apparatus in accordance with the invention, generally designated 10, comprises a microwave generator, similar to conventional microwave ovens and schematically shown at 12, having a rotating table 14 located within the microwave cavity 16. A dental handpiece 18 to be sterilized is situated within a sealed, flexible or collapsible pouch 20 along with a predetermined quantity of liquid sterilant solution 22 to form a gas-tight assembly 24. The collapsible pouch 20 is designed with minimal volume preferably sufficient to accommodate only a single dental handpiece and is formed of sheet material which is transparent to microwave radiation and impermeable to the vapor of the liquid sterilant solution. In a preferred embodiment, the liquid sterilant solution comprises 2 ml. of glutaraldehyde solution and the pouch 20 is formed of sheet material having a thickness of about 2 mils and comprising a laminate of polyester and polyethylene. A predetermined amount of liquid sterilant solution 22 is introduced through an opening into the pouch 20 along with the dental handpiece 18 whereupon the opening is sealed to form the gas-tight assembly 24. The gas-tight assembly 24 comprising the collapsible pouch in which the dental handpiece 18 and liquid sterilant solution 22 is placed on the rotating table 14 within the cavity 16 of microwave generator 12 and subjected to microwave irradiation. As the microwave radiation continues, the liquid sterilant solution 22 is vaporized under the thermal effects of the microwave radiation producing a hot sterilant vapor. In accordance with the invention the quantity of liquid sterilant introduced into the collapsible pouch is sufficient so that upon vaporization, an overpressure is created within the pouch 20. That the required overpressure has been achieved is visually apparent according to the invention by observation of the walls 26 of pouch 20 which flex outwardly from their initially collapsed condition (see FIG. 2) under the forces of the increasing internal pressure and reach a fully distended condition, designated 26', in FIG. 3, upon the internal pressure reaching the minimum or lower overpressure requirement. The hot sterilant vapor contacts the surfaces of the dental handpiece 18 under pressure penetrating into the narrow seams and crevices thereof. At the same time, the dental handpiece 18 is subjected to microwave irradiation. The microwave irradiation is continued for a certain time with the dental handpiece in the radiation field and in the atmosphere of the hot sterilant vapor under pressure until the handpiece has been sterilized. Sterilization of the handpiece 18 is therefore achieved by the thermal and non-thermal effects of the microwave radiation as well as by chemical vapor treatment.

Tests using a conventional, commercially available 500 watt microwave oven and the arrangement described above have shown that a dental handpiece contaminated with bacterial spores, in particular spores of Bacillus-Stearothermophilus, was effectively sterilized, i.e., all of the spores were killed, in only five minutes. It will be appreciated that spores of this bacillus are extremely difficult to kill and are generally used to test sterility effectiveness of steam autoclaves. No arcing or sparking of the handpiece caused by microwave radiation was observed when the handpiece was so irradiated in the atmosphere of the hot sterilant vapor under pressure.

The rotating table 14 is utilized in order to obtain a uniform irradiation of the gas-tight assembly 24. Of course, this can be dispensed with if the particular microwave radiator employed provides a uniform radiation field within the cavity.

It is desirable to minimize the volume of the collapsible pouch 20 to reduce sterilization cycle time. Since different articles to be sterilized have different geometries, a preferred construction of pouch 20 will permit a "custom design" by the practitioner or his staff for a particular instrument for mimimizing the internal volume of the gas-tight assembly. In this connection, referring to FIGS. 4-6, the pouch 20 is formed from 2-ply web material 28 of constant width, preferably maintained and made available to the practitioner in the form of a roll 30. The web material 28 comprises a pair of overlying elongate sheets of polyester-polyethylene laminate whose outer edge margins 38 have been previously sealed to each other to form a tubular construction. A section 34 of the tubular web material 28 is cut from roll 30 along the line 36, the section having a length L which is somewhat greater than that required to accommodate the instrument, namely, the dental handpiece 18, to be sterilized. One of the open ends 38 of the web material section 34 is sealed by fusing the overlying sheets to each other along a transverse seal line 40 by a hot-wire sealing apparatus 42 (FIG. 5). The seal apparatus 42 comprises a fixed, heated resistance wire 44 mounted on and extending across a housing 46 an a counter-member 48 formed of a rubber-type material fixed to a cover member 50 pivotally connected to housing 46 in a position so as to come into registering alignment with wire 44 when cover member 50 is pivoted to its closed position. A series of transversly aligned perforations 52 are formed through the sealed outer edge margins 32 of the web 2 and pair of locating pegs 54 spaced from each other by a distance equal to the distance between each pair of transversely aligned perforations 52 are provided in front of resistance wire 44.

The construction of the gas-tight unit 24 proceeds as follows. After cutting tubular web section 34 from roll 30, a pair of transversely aligned perforation 52 proximate to end 38 are located over the peg 54 such that an end region of the tubular web section 34 overlies the heated resistance wire 44. The cover member 50 of apparatus 42 is closed whereby the counter-member 48 urges the overlying sheets of tubular web 28 against each other and against the heated resistance wire 44 whereupon the sheets are fused to each other to form the transverse seal line 40 and thereby the collapsible pouch 20. The dental handpiece 18 and about 2 ml of the liquid glutaraldehyde sterilant solution 22 are introduced into pouch 20 through opening 56. The opening 56 is then sealed using the hot-wire sealing apparatus 42 in the same manner as described above to form a second transverse seal line 58 (shown in phantom in FIG. 6) proximate to the end 60 of section 34 thereby forming the sealed, gas-tight assembly 24.

The above described arrangement for constructing the gas-tight assembly 24 is advantageous in that it is simple and fast. Moreover, the volume of the gas-tight assembly is custom designed for the particular instrument being sterilized, on the one hand, being sufficient to accommodate the instrument, and on the other hand, being minimized to the extent possible to reduce the quantity of liquid sterilant solution required to achieve the desired internal overpressure upon vaporization, and in turn to decrease the amount of time required to vaporize the liquid sterilant solution, and, therefore, the overall sterilization cycle time. The equipment required for constructing the collapsible pouch is simple, inexpensive and readily available. The pouches are disposable after the sterilization treatment has been completed and the dental handpiece can be stored in the gas-tight assembly until its use is required. The sterilization treatment is odorless and does not cause irritation of the eyes, nose or throat. The microwave cavity 16 need not be cleaned since the sterilant vapor is contained within the gas-tight assembly 24. Importantly, the instrument 18 is completely sterilized in a very short time.

It is advantageous to utilize microwave energy for vaporizing the liquid sterilant solution within the collapsible pouch in the chemical vapor sterilization technique of the invention because of the efficiency of its thermal effects and the ready availability of microwave generators. However, although arcing is not a problem in the combined microwave and chemical vapor sterilization of a single dental handpiece, as described above, it would not normally be possible to simultaneously sterilize a plurality of instruments situated in the same collapsible pouch or even a single instrument having a sharp point or edge in the manner described above using microwave energy to vaporize the liquid sterilant solution in the gas-tight assembly without risking the potential for arcing or sparking to occur.

In accordance with another aspect of the invention, referring to FIGS. 7-9, an arrangement is illustrated by which a simultaneous chemical vapor sterilization of a plurality of instruments 62 situated in the same collapsible pouch 20 is accomplished utilizing microwave energy to vaporize the liquid sterilant solution 22 without the risk of arcing or sparking. More particularly, the instruments 62 are initially inserted into the interior of a shield assembly 64 (FIG. 7) which comprises a tubular holder member 66 formed of an electrically insulative material, such as plastic, preferably having a plurality of apertures 67 formed therethrough. The outer surface of tubular member 66 is covered by an electromagnetic radiation shield material 68. Shield material 68 may comprise, for example, a double layered knitted mesh of tin-copper-steel wire effective in shielding microwave radiation available in strip form from the Tecknit Company of Cranford, N.J. under the designation EMC Shielding Tape. In this example, the shield assembly 64 comprises a tubular shield assembly including the apertured tubular member 66 over the outer surface of which a strip of the knitted wire mesh 68 is wrapped. The instruments 62 are sterilized by initially inserting them into the interior of the tubular member 66 of the shield assembly 64 whereupon the shield assembly and instruments contained therein are introduced into a collapsible pouch 20 along with a quantity liquid sterilant solution 22 whereupon the pouch is sealed to form a gas-tight assembly 24 as described above. The gas-tight assembly is irradiated by microwave energy whereupon the liquid sterilant solution is vaporized by the thermal effects of the microwave radiation and the hot chemical vapor under pressure flows through the mesh and apertures 67 of tubular member 66 into contact with the surfaces of instruments 62 to sterilize the same. No sparking or arcing occurs.

Although perhaps not as advantageous as the embodiment of the invention wherein an instrument is sterilized under the combined effect of chemical vapor and microwave radiation, it will be understood that sterilization can be accomplished according to the invention using only the chemical vapor under pressure arrangement of the invention in the absence of microwave radiation. For example, referring to FIG. 10, the gas-tight assembly 24 of FIG. 2, including a collapsible pouch in the interior of which is sealed an instrument to be sterilized and an appropriate quantity of liquid sterilant solution, is situated in the interior of an infrared radiator device 86 in which a rod-shaped infrared radiator 88 is provided. Elliptical mirrors 90 are provided within the infrared radiator device 86 defining a pair of vocal lines for the infrared radiation emitted from radiator 88. The infrared radiator 88 is positioned on the first focal line and the gas-tight assembly is situated in a simple holder device 92 at the second focal line. When the radiator 88 is activated, a high beam concentration of the infrared radiation is focused onto the gas-tight assembly 24 rapidly vaporizing the liquid sterilant solution to sterilize the instrument by chemical vapor as described above.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. A method for sterilizing at least one article by vapor under pressure comprising the steps of:
    introducing at least one article to be sterilized and a quantity of liquid into a collapsible pouch formed of material at least partially transparent to radiation through a sealable opening therein, said quantity of liquid being sufficient so that when said pouch opening is sealed to form a gas-tight assembly and said liquid is vaporized, an overpressure is created within said pouch which will expand said pouch to a visually-apparent distended condition;
    sealing said pouch opening to form a gas-tight assembly; and
    irradiating said gas-tight assembly with said radiation while shielding said at least one article from said radiation to vaporize said liquid so that said collapsible pouch expands to a visually-apparent distended condition to produce an atmosphere of hot vapor under pressure in said gas-tight assembly, while shielding said at least one article from said radiation,
    whereby said at least one article situated within said gas-tight assembly is sterilized under the effect of vapor under pressure.

2. The method recited in claim 1 wherein said collapsible pouch is formed of plastic sheet material and said step of sealing said pouch opening to form a gas-tight assembly comprises the step of fusing narrow transversely extending regions of overlying sheet portions of said pouch to each other.

3. The method recited in claim 1 wherein said collapsible pouch has an interior volume sufficient to accommodate only a single article to be sterilized.

4. The method recited in claim 1 wherein said radiation comprises microwave radiation.

5. The method recited in claim 1 including the preliminary step of constructing a collapsible pouch by
    forming a section of tubular web from a pair of overlying sheets of plastic material sealed at their longitudinal side edges; and
    sealing one of the ends of said tubular web section by fusing first narrow transversely extending regions of said overlying sheets proximate to one of said ends to each other.

6. The method recited in claim 5 wherein said tubular web section is formed by severing a length of said tubular web from a roll thereof.

7. The method recited in claim 1 wherein said at least one article is shielded from said radiation by positioning said at least one article within a space substantially surrounded by shielding means for providing a barrier to the transmission of said radiation.

8. The method recited in claim 7 wherein said space comprises the interior of a holder member having wall means defining said space, said space being open to the ambient atmosphere, and wherein said shielding means are provided over at least a part of said holder member well means.

* * * * *